(12) United States Patent
Lustenberger et al.

(10) Patent No.: US 7,508,505 B2
(45) Date of Patent: Mar. 24, 2009

(54) APPARATUS AND METHOD FOR ALL-SOLID-STATE FLUORESCENCE LIFETIME IMAGING

(75) Inventors: Felix Lustenberger, Cham (CH); Thierry Oggier, Zurich (CH); Alessandro Esposito, Gottingen (DE); Fred Silvester Wouters, Gottingen (DE)

(73) Assignees: Mesa Imaging AG, Zurich (CH); Carl Zeiss Microimaging GmPH, Jena (DE)

( * ) Notice: Subject to any disclaimer, the term of this patent is extended or adjusted under 35 U.S.C. 154(b) by 250 days.

(21) Appl. No.: 11/490,482

(22) Filed: Jul. 20, 2006

(65) Prior Publication Data
US 2007/0018116 A1  Jan. 25, 2007

(30) Foreign Application Priority Data
Jul. 21, 2005  (EP)  ................................. 05015860

(51) Int. Cl.
*G01J 3/30*  (2006.01)
(52) U.S. Cl. ................ 356/317; 250/208.1; 250/214 R; 250/214.1; 250/458.1
(58) Field of Classification Search .............. 250/208.1, 250/214 R, 214.1, 458.1; 257/443
See application file for complete search history.

(56) References Cited

U.S. PATENT DOCUMENTS

| | | | |
|---|---|---|---|
| 5,459,323 A | | 10/1995 | Morgan |
| 7,034,317 B2* | | 4/2006 | Olszak et al. ............ 250/458.1 |
| 7,279,338 B2* | | 10/2007 | Kim et al. .................... 436/177 |
| 2001/0035568 A1* | | 11/2001 | Shyu ........................... 257/666 |
| 2004/0008394 A1* | | 1/2004 | Lange et al. ................. 359/237 |
| 2004/0028567 A1* | | 2/2004 | Parce et al. .................. 422/100 |
| 2005/0023439 A1* | | 2/2005 | Cartlidge et al. .......... 250/208.1 |

FOREIGN PATENT DOCUMENTS

| | | |
|---|---|---|
| EP | 0 911 667 | 4/1999 |
| EP | 1 162 827 | 12/2001 |
| EP | 1 746 410 A1 | 1/2007 |
| WO | WO 02/12945 | 2/2002 |

OTHER PUBLICATIONS

"Fluorescence Lifetime Imaging Microscopy", Alessandro Esposito and Fred S. Wouters, Current Protocols in Cell Biology, 2004.

(Continued)

*Primary Examiner*—Kara E Geisel
*Assistant Examiner*—Abdullahi Nur
(74) *Attorney, Agent, or Firm*—Weingarten, Schurgin, Gagnebin & Lebovici LLP

(57) ABSTRACT

Fluorescence lifetime imaging microscopy (FLIM) is a powerful technique increasingly used in the life sciences during the past decades. An all-solid-state fluorescence-lifetime-imaging microscope (1) with a simple lock-in imager (4) for fluorescence lifetime detection is described. The lock-in imager (4), originally developed for 3D vision, embeds all the functionalities required for FLIM in a compact system. Its combination with a light-emitting diode (2) yields a cost-effective and user-friendly FLIM unit for wide-field microscopes. The system is suitable for nanosecond lifetime measurements and achieves video-rate imaging capabilities.

11 Claims, 3 Drawing Sheets

OTHER PUBLICATIONS

"Measurement of Nanosecond Time-Resolved Fluorescence with a Directly Gated interline CCD Camera", A.C. Mitchell, J.E. Wall, J.G. Murray and C.G. Morgan, Journal of Microscopy, vol. 206, pp. 233-238, 2002.

"Real-Time Lock-In Imaging by a Newly Developed High-Speed Image-Processing Charge Coupled Device Video Camera", Kentarou Nishikata, Yoshihide Kimura and Yoshizo Takai, American Institute of Physics, 2003.

An All-Solid-State Optical Range Camera for 3D Real-time Imaging with Sub-Centimeter Depth Resolution (SwissRanger™), Thierry Oggier et al., CSEM SA, Badenerstrasse 569, CH-9048 Zurich, The Royal Microscopial Society, Journal of Microscopy, 2002.

"Direct Modulation of the Effective Sensitivity of a CCD Detector: a New Approach to Time-Resolved Fluorescence Imaging", A.C. Mitchell et al., the royal Microscopial Society, 2002.

Elson, D.S.: "Fluorescence lifetime system for microscopy and multiwell plate imaging with a blue picosecond diode laser," Optics Letters, vol. 27, No. 16, 2002, pp. 1409-1411.

Seitz, P.: "CSEM Scientific and Technical Report 2003" [Online] 2003. Retrieved from the Internet: URL:http://www.csem.ch/corporate/Report2003/pdf/photonics_03.pdf> [retrieved on Mar. 21, 2006] p. 45.

Webb, S.E.D., et al: "A wide-field time-domain fluorescence lifetime imaging microscope with optical sectioning," Review of Scientific Instruments, American Institute of Physics, US, vol. 73, No. 4, Apr. 2002, pp. 1898-1907.

Elson, D.: "Time-domain fluorescence lifetime imaging applied to biological tissue," Photochem. Photobiol. Sci., 2004, pp. 795-301.

Hess, H., et al., "PMD—New Detector for Fluorescence Lifetime Measurement," Proceedings from Int. Conference Optoelectronics, Optical Sensors and Measuring Techniques, May 2002, 6 pages.

\* cited by examiner

APPARATUS AND METHOD FOR ALL-SOLID-STATE FLUORESCENCE LIFETIME IMAGING

This application claims priority to European application No. EP 05 015 860.9 filed Jul. 21, 2005.

FIELD OF THE INVENTION

This invention is in the field of time-resolved measurements of luminescence, i.e., fluorescence, phosphorescence and the like, and especially fluorescence lifetime imaging microscopy (FLIM). It relates to an apparatus and a method for imaging a luminescent sample, according to the preambles of the independent claims.

BACKGROUND OF THE INVENTION

The fluorescence or luminescence lifetime is the average time that a fluorochrome spends in the excited state. The sensitivity of the fluorescence (or luminescence) lifetime to environmental factors can be exploited to investigate the physico-chemical environment of fluorochromes. From the early 1990s, fluorescence lifetime imaging microscopy (FLIM) allowed the quantitative and robust imaging of pH, ion concentration, oxygen content, etc., in living cells, tissues and model organisms. Moreover, FLIM enabled protein-protein interactions to be mapped in cells, by imaging the occurrence of the phenomenon of Förster Resonance Energy Transfer (FRET).

However, even given its intrinsic value, the spreading of FLIM instrumentation in laboratories is limited by its cost and by the required know-how necessary for its maintenance and operation. More recently, the use and value of FLIM for diagnostic applications, histology and screening has been demonstrated. Thus, the establishment of cost-effective and user-friendly systems is a requirement to allow its widespread application in laboratories and research fields.

Both the detection of lifetimes in the time-domain (TD) and in the frequency-domain (FD) regime, and the use of laser scanning (LSM) and wide-field microscopy have been widely described in literature. In the time domain, the donor molecule is excited with a pulsed light source and the fluorescence intensity decay is recorded as a function of time. Because the fluorescence lifetimes of typically used organic and genetic fluorophores range in the low nanosecond region, pico- or femto-second pulsed sources and repetition rates in the megahertz range are required. These light sources can also be used in the frequency domain. More often, FD uses sinusoidally modulated light sources. FD detection allows the use of higher illumination duty cycles, thereby permitting the fastest acquisition times. The major advances in solid-state technologies today enable the use of cost-effective laser diodes (LDs) and inexpensive light emitting diodes (LEDs) as directly modulated light sources. The former can be pulsed in the pico-second range, albeit at the cost of reduced laser operation lifetime and subsequent operation costs. LEDs can be pulsed in the nanosecond range, sufficient to obtain fluorescence lifetime information, but are not ideal for the robust and efficient measurement of nanosecond or sub-nanosecond decays. On the other hand, both LDs and LEDs can be intensity-modulated in the MHz region, the optimal frequency range for the frequency-domain detection of nanosecond decaying fluorochromes. Luminescent probes exhibit lifetimes in the microsecond to millisecond range, thus posing less stringent technological requirements. LDs and LEDs are increasingly replacing expensive continuous-wave lasers that are modulated by external optical devices, and mode-locked lasers.

The detectors used for laser-scanning and wide-field microscopes differ substantially (Esposito A. and Wouters F. S., "Fluorescence Lifetime Imaging Microscopy", In: Current Protocols in Cell Biology; Bonifacino J. S., Dasso M., Harford J. B., Lippincott-Schwartz J., and Yamada K. M., editors, 2004). The former use sensitive and fast point detectors like photo-multiplier tubes (PMTs), multi-channel-plate PMTs (MCP-PMTs), avalanche photodiodes (APD) or single photon counting APDs (SPADs) in the various detection techniques: time-correlated single-photon-counting (TCSPC) and time-gated (TG) detection in the TD, and cross-correlation for FD operation. Wide-field detection requires the use of a spatially-resolved MCP detector. MCPs are relatively expensive, prone to photo-damage and require elaborate electronics for operation. Moreover, although the time properties of MCPs are optimal, their spatial resolution is relatively low, they can present "chicken-wire" artifacts caused by the fiber-optic coupling to CCD pixels, and can inject a relatively high noise level in the measurement. For these reasons, a robust solid-state detector presents a desirable alternative to multi-channel-plates for routine FLIM application by a larger user community and also for application in medical diagnostics and high-throughput pharmacological compound screening. Therefore, the detector of the invention does not require the use of a multi-channel-plate for the signal demodulation.

The sensitivity or photoeconomy of FLIM systems has been described by the use of the ratio (F value) of the coefficient of variation of the lifetime image and the intensity map. The combination of a scanning system and femtosecond-laser sources with detection in the time domain (TCSPC) or frequency domain (lock-in) has been shown to have F values close to unity, i.e., the maximally achievable photoeconomy. The use of an MCP for wide-field detection deteriorates this performance. Under sine-ve illumination and detection with three images at different phases, the F values reach a value higher than 7, i.e., approx. 50 times more photons have to be collected to achieve a signal-to-noise ratio equal to a system that uses a femtosecond laser and an MCP-PMT as the detector system. A lock-in imager can offer higher sensitivity than an MCP. The combination of solid-state technologies, frequency-domain detection and wide-field microscopy seems to be a good compromise in terms of cost and simplicity of use.

In the recent past, pioneering works have been published (Mitchell A. C., Wall J. E., Murray J. G., and Morgan C. G., "Direct modulation of the effective sensitivity of a CCD detector: a new approach to time-resolved fluorescence imaging", Journal of Microscopy, Vol. 206, Pt. 3, 225-232, 2002; Mitchell A. C., Wall J. E., Murray J. G., and Morgan C. G. "Measurement of nanosecond time-resolved fluorescence with a directly gated interline CCD camera", Journal of Microscopy, Vol. 206, Pt. 3, 233-238, 2002; Nishikata K., Kimura Y., Takai Y., Ikuta T., and Shimizu R., "Real-time lock-in imaging by a newly developed high-speed image-processing charged coupled device video camera", Review of Scientific Instruments, 1393-1396, 2003) that aimed at the use of charged-coupled-devices (CCDs) in FLIM. They reported on the possible modification of a commercial CCD camera to allow lifetime detection. Their theoretical upper limit was estimated at approximately 10 MHz, but a realistic practical implementation was demonstrated to be feasible at a lower modulation frequency of 500 kHz. These modulation frequencies are sub-optimal for use with typically used fluorophores in life sciences.

By the same token, EP-1'162'827 A2 teaches the use of CCDs for time-resolved measurements of luminescence. For this purpose, conventional CCD arrays are described in which charges are moved bi-directionally from one pixel to another, or in which the spatial extent of charge collection from pixels is controlled.

On the other hand, CCD lock-in imagers are commercially produced for time-of-flight (TOF) ranging (Oggier T., Lehmann M., Kaufmann R., Schweizer M., Richter M., Metzler P., Lang G., Lustenberger F., and Blanc N., "An all-solid-state optical range camera for 3D real-time imaging with sub-centimeter depth resolution (SwissRanger™)", Proc. of SPIE Vol. 5249, 534-545, 2004). The field of TOF ranging is completely different from the field of microscopy. The former deals with large objects lying far away (in distances of several meters or more); knowledge of electric engineering and microelectronics is required. In the latter, small objects lying under a microscope are investigated, for which experiences in life sciences and in optics are needed. To date, these two technical fields have not overlapped.

SUMMARY OF THE INVENTION

It is an object of the present invention to provide an apparatus and a method for imaging a luminescent sample that are fast and at the same time more cost-effective and more user-friendly than the systems known from the prior art.

These and other objects are solved by the apparatus and the method as defined in the independent claims. Preferred embodiments are indicated in the dependent claims.

The present invention is based on the recognition that all-solid-state lock-in imagers are a valid alternative to MCP detection in FLIM. Thus, it uses a CCD/CMOS hybrid lock-in imager originally developed for full-field 3D vision in real time, using the TOF detection principle, as an imaging device on a FLIM. This technology, currently operating at a modulation frequency of 20 MHz, is expected to work at higher frequencies up to 100 MHz.

The invention shows how an all-solid-state wide-field frequency-domain FLIM can be implemented for the imaging of fast fluorescence decays and, moreover, can be operated at video rate. It provides a fast, cost-effective and user-friendly FLIM system.

The use of a lock-in imager for lifetime imaging has experimentally been demonstrated. The results presented below represent the lowest performance that can be achieved with the current camera system. Actually, the state-of-the-art of solid-state lock-in imaging devices, when specifically adapted for fluorescence detection, should significantly outperform our currently presented results. The optical performance of the current system can be easily improved by some adaptations: its sensitivity can be improved by a better optical fill factor (~50%) in a new design of the detection chip, the use of micro-lens arrays (~300%) and dedicated optics for the optical coupling (~50%). Proper cooling and high-end electronics will significantly lower the noise level in lock-in imaging (~100%), with modulation intensities up to 100 MHz and at speeds up to 30-50 frames per second. The removal of the dark current, which currently can easily approach half of the signal range, limits both sensitivity and exposure time. With reduced or even eliminated dark current, longer exposures become possible with concomitant improvements of sensitivity and noise characteristics. Therefore, a redesign of the existing ranging camera, using readily available components and techniques, will allow the full extension of its application to FLIM. These improvements could generate a system which even outperforms the current multi-channel-based detection, thereby obviating the need for this excessively expensive electro-optical component in lifetime imaging.

Monte-Carlo simulations of the lock-in imager and the application of the Rapid Lifetime Determination (RLD) algorithm indeed show that the F value of such a detection system approaches unity when Dirac excitation is used. This performance is only slightly deteriorated when a duty cycle equal to 20% is used, i.e., 10 ns pulses at 20 MHz of modulation frequency. A pulse width between 2 and 4 ns was demonstrated to be feasible with LEDs. Furthermore, under a sine excitation regime, the lock-in imager offers F values equal to approximately 2.6, allowing the use of 7-fold reduction of photons compared to the use with an MCP.

The inventive apparatus for imaging a luminescent sample comprises a radiation source arranged to illuminate the sample with excitation radiation, modulation means for modulating an intensity of the excitation radiation, detector means, comprising a plurality of pixels, for detecting luminescent radiation emitted by the sample, and control means for controlling the mutual phase relation of the radiation source and the detector means. At least one pixel of the detector means comprises a radiation-sensitive element for converting incident radiation into an electric signal, at least one storage element for storing the electric signal, and transfer means for transferring the electric signal from the radiation-sensitive element to a selected one of the storage elements. The pixel may comprise at least one storage element and one dump element or a plurality of storage elements for storing or dumping the electric signal. The apparatus further comprises readout means for individually reading out the electric signal stored in the at least one storage element of said at least one pixel.

The inventive method for imaging a luminescent sample comprises the steps of: illuminating the sample with excitation radiation intensity-modulated with a modulation frequency, and periodically detecting in a plurality of pixels luminescent radiation emitted by the sample, synchronously with the modulation frequency of the intensity-modulated radiation. The detection step comprises the partial steps of: converting incident radiation into an electric signal, providing at least one storage element in at least one pixel, selecting one of the at least one storage element, storing the electric signal in said selected storage element, and individually reading out the electric signals stored in the at least one storage element of said at least one pixel.

It has been demonstrated that a lock-in imager can detect contrast and correct absolute fluorescence lifetimes of short lifetime fluorophores, including genetically expressed green fluorescent protein (GFP) variants that are commonly used in the life sciences. Furthermore, an all-solid-state wide-field FLIM in the frequency-domain with the use of an LED and an LD illumination and a CMOS/CCD lock-in imager has been developed. Additional electronics, i.e., the power amplifier and the bias-tee for driving the LED, were only necessary to match the camera signals to the electrical properties of the LEDs utilized in the experiments.

Routinely, FLIM is performed with low pixel resolution of typically 256×256 pixels for most commercial TD systems to avoid long integration times with laser scanning microscopes or excessive over-sampling of the MCP-camera output. Increasing spatial resolution comes at the cost of lower photon counts per pixel, and thus the deterioration of the FLIM signal. However, this resolution can be easily increased as it is not dictated by technological limits and, given the wide-field nature of the detection, will allow frame rates similar to the current implementation. In fact, we demonstrate the powerful combination of the lock-in imager with the RLD algorithm for FD. The parallel acquisition of the solid-state camera removes the photo-bleaching and sample-motion artifacts the RLD suffers from during sequential acquisition. This allows the robust imaging of lifetimes at video rate. Moreover, the use of the efficient (lower F-values) RLD can allow lock-in imagers to operate at lower light intensities.

The invention will allow the implementation of FLIM systems with lower cost, higher time resolution, better noise characteristics and operable in real time at video rate. The systems can be reasonably featured with typical optical sensitivity of CCD, CMOS/CCD or CMOS imagers, 256×256 or 512×512 pixel resolutions, working in a variable frequency range between 5 MHz and 100 MHz, containing all necessary electronics on board, and easy to use as a standard camera even by non-specialist operators.

Summing up, it can be said that FLIM is a powerful technique that is increasingly being used in the life sciences during the past decades. FLIM allows the enhancement of image contrast, the investigation of the physicochemical environment of fluorochromes and the mapping of protein-protein interactions. However, a broader application of the technique requires more cost-effective and user-friendly solutions. Wide-field frequency-domain FLIM represents a solution whose wide-spread application is currently limited by the use of multi-channel-plate image intensifiers. According to the invention, a simple lock-in imager is used for fluorescence lifetime detection. The lock-in imager, originally developed for 3D vision, embeds all the functionalities required for FLIM in a compact system. Its combination with light emitting diode or solid-state laser light sources demonstrates the possibility to build a cost-effective and user-friendly FLIM unit for wide-field microscopes. The system is suitable for nanosecond lifetime measurements. The combination of fast lock-in CCD/CMOS imagers with solid-state light sources can bridge the technological divide that limits the use of FLIM in relevant areas that could benefit from its application. Furthermore, it allows a robust use of the efficient rapid lifetime determination algorithm, achieving video-rate imaging capabilities.

Apart from FLIM, the invention encompasses the use of a lock-in imager for any time-resolved application that makes use of wide-field detection. Examples are Nipkov-disk based confocal microscopes, structured illumination detection or spectrally resolved microscopes. In fact, Nipkov-disk confocal microscopes, programmable-array microscopes (cf. EP-0'911'667) and other structured illumination based applications like the ApoTome by Carl Zeiss AG (cf. WO-02/12945) exhibit high spatial resolution and sectioning capabilities and require a wide-field detection system that can be combined with lifetime detection according to the invention. Spectrally resolved microscopes have been described that make use of CCD detectors. Here, a pixel or line-scanning microscope generates luminescent light that is divided into its spectral components by means of a prism, a grating or by any other means. The light is then integrated in time on a CCD, CMOS or combined CMOS/CCD camera. With a point illumination, the emitted light is spectrally separated and collected in a line or ensemble of CCD or CMOS imager lines which can be read out to retrieve the different spectral components of fluorescence species in the sample. With a line-scanning microscope, the spectral separation of the emitted light generates a bi-dimensional pattern containing a spatial and a spectral dimension. In this case, the use of wide-field detection allows comparatively fast spectral imaging. The integration of the lock-in imager with such a technique will therefore allow fast time-resolved spectral imaging.

The apparatus and/or the method according to the invention can be used, e.g., in biotechnological or medical applications. Such applications may be medical diagnostics, the study of biological components in vitro within cells, tissues or model organisms, or the screening, preferably high-throughput screening, of pharmacological compounds.

BRIEF DESCRIPTION OF THE DRAWINGS

Embodiments of the invention are described in greater detail hereinafter relative to the attached schematic drawings.

DESCRIPTION OF PREFERRED
EMBODIMENTS

Figure 1:
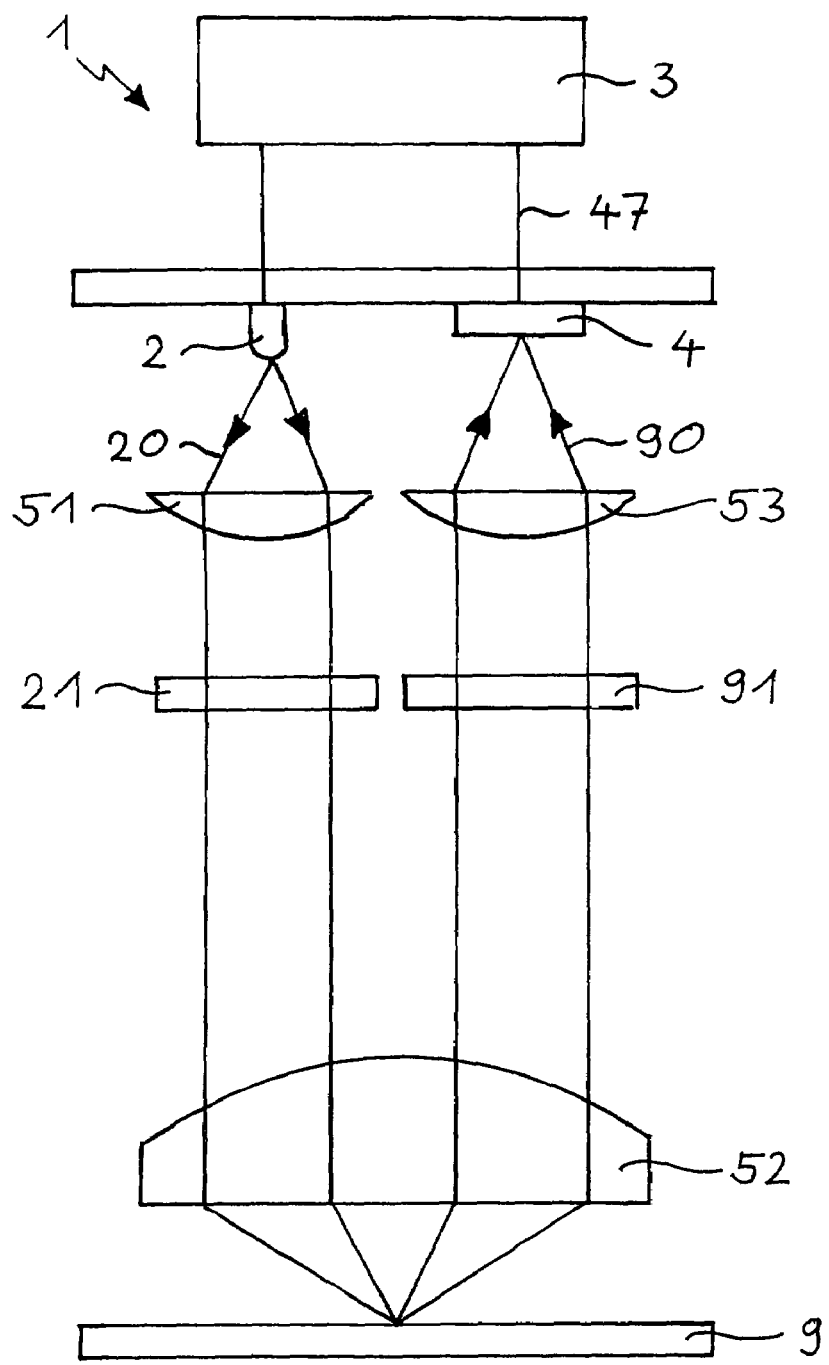
FIG. 1 shows trays of the rays in a FLIM according to the invention.

FIG. 1 schematically shows important components of the FLIM 1 according to the invention and trays of the rays therein. In an experiment, a fully automated Axiovert200M microscope (Carl Zeiss Jena GmbH, Jena, Germany) was used as the base of the FLIM 1, the necessary adaptations having been made thereto. Excitation light 20 is provided by a light source 2 modulated at a modulation frequency of, e.g., 20 MHz. The light source 2 may be, e.g., a solid-state Compass laser (Coherent Inc., Santa Clara Calif., USA) emitting light 20 at a wavelength of 405 nm, or an NSPB500S LED (Nichia Corp., Japan) peaked around 470 nm. In the latter case, the excitation light 20 is preferably filtered through an excitation filter 21. The excitation light 20, collimated by a collimating lens 51 and filtered by the excitation filter 21, is directed towards a probe 9. In an experiment, the probe 9 was turbo-sapphire (TS) green fluorescent protein. A lens 52 of the microscope is used for focusing the excitation light 20 onto the probe 9 as well as for imaging the probe 9. Fluorescent light 90 emitted by the probe 9 passes through the lens 52 and a detection filter 91, e.g., an optical band-pass filter transmitting at 515±30 nm. A lock-in imager 4 of the CCD/CMOS type (cf. FIG. 2) is used for acquiring the fluorescence emission 90 and is preferably arranged behind an optical output port 53 of the microscope. The lock-in imager 4 may be mounted on a binocular port of the microscope by means of a 0.4×C-mount adapter. The light source 2 and the lock-in imager 4 are driven by driving circuitry 3 that may comprise a signal generator, control means for controlling the mutual phase relation of the light source 2 and the lock-in imager 4, and other elements.

The FLIM 1 further comprises readout means 47 for individually reading out the electric output signals from the individual pixels of the lock-in imager 4. Such readout means 47 are known from conventional active-pixel-sensor (APS) architecture and may comprise row select transistors in each pixel, signal lines for controlling the row select transistors, signal buses in column direction, corresponding output lines, a row address decoder, a column address decoder and/or a readout circuit; in FIG. 1, the readout means 47 are indicated only diagrammatically. The driving electronics 3, the light source 2, the lock-in imager 4 and the readout means 47 are preferably integrated on one single circuit board. The FLIM 1 may be calibrated by imaging a reflective foil or other scattering media as zero lifetime reference or a fluorescent sample of known lifetime.

Figure 2:
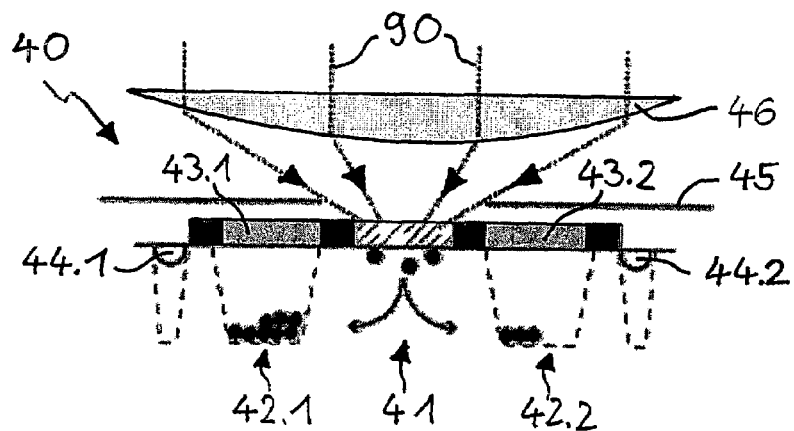
FIG. 2 shows a cross-section through a pixel of a FLIM according to the invention.

FIG. 2 shows a schematic cross-section through a pixel 40 of the lock-in imager 4 (cf. FIG. 1). Potential distributions (as functions of the transverse coordinate) and photoelectrons are also schematically indicated. The pixel 40 has a photosensitive region 41 that converts incident light 90 into photoelectrons. The photoelectrons can be collected and integrated in two distinct storage sites 42.1, 42.2, depending on the potentials or electric signal waveforms applied to corresponding gate electrodes 43.1, 43.2. In the example of FIG. 2, the integrations are performed at opposite phases. This allows the cross-correlation and read-out of two images, acquired simultaneously within one period at opposite phases. A sense node 44.1, 44.2 to which the integrated photoelectrons can be transferred is allocated to each integration gate 42.1, 42.2. The sense nodes 42.1, 42.2 are contacted by corresponding readout lines, which are known from the prior art and not shown in FIG. 2. All pixel structures 42.1, 42.2, 43.1, 43.2, 44.1, 44.2 except the photosensitive region 41 are preferably shielded from the incident light 90, which is indicated in FIG. 2 by an opaque light shield 45. A micro-lens array 46 arranged on top of the lock-in imager 4 may improve the quality of the FLIM images acquired.

Figure 3A:
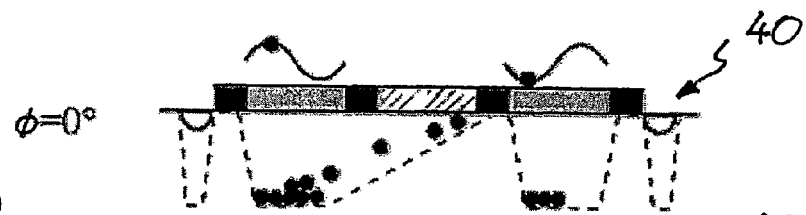
FIG. 3 shows cross-sections through a pixel of a FLIM according to the invention for three different potentials applied to the integration gates.
Figure 3B:
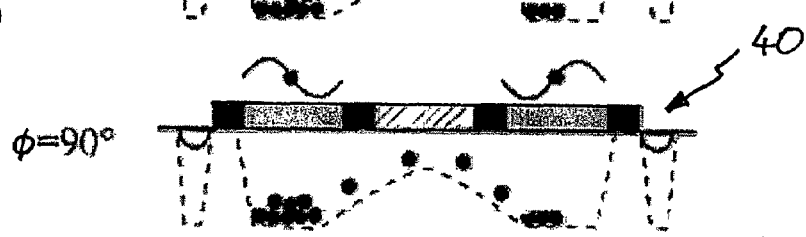
Figure 3C:
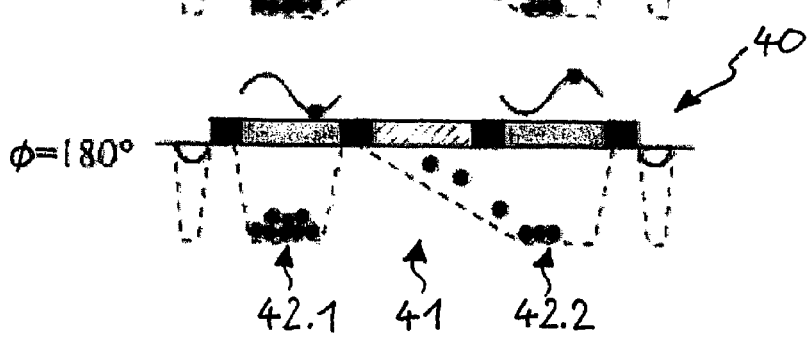

For the signal detection, a sequential acquisition of four images at relative phases of 0°, 90°, 180° and 270° ($I_{0°}$, $I_{90°}$, $I_{180°}$, and $I_{270°}$ respectively, called 1-tap), a simultaneous capture of two images at opposite phases ($I_{0°}$, $I_{180°}$, called 2-tap) or even a simultaneous acquisition of the four relative phases (called 4-tap) is preferably used. The 2-tap case is illustrated in FIG. 3. Those skilled in the art can easily extend the measurement principle to n-tap behavior, where n>0 is an integer. Two time-dependent bias voltages are applied to the gate electrodes 43.1, 43.2 (cf. FIG. 2) of the pixel 40. The applied bias voltages are each modulated with the modulation frequency of the excitation light 20 (cf. FIG. 1), but shifted by a phase shift of 180° with respect to each other. The pixel 40 is shown for three moments during one modulation period, corresponding to the three phases $\phi=0°$, 90° and 180°. Depending on the bias voltages applied to the integration gates, the photo-generated electrons are stored in the first integration gate 42.1 (FIG. 3(a), $\phi=0°$) or in the second integration gate 42.2 (FIG. 3(c), $\phi=180°$). Between these clearly defined moments, transitional states occur during which the photo-generated electrons are stored in both integration gates 42.1, 42.2 (FIG. 3(b), e.g., $\phi=90°$ or 270°).

The sequential acquisition of four images at relative phases 0°, 90°, 180° and 270° (called 1-tap approach) has a very similar architecture as the 2-tap version described in FIG. 2 and 3, but instead of implementing two storage elements 42.1, 42.2 there is only one storage element 42.1 on each pixel, and the second storage element 42.2 is replaced by an electron-dumping element (not shown), e.g., a dump diffusion. By replacing one integration gate 42.2 and one readout node 44.2 by a dumping element, the pixel size can be reduced. The drawbacks of the 1-tap pixel are (a) that half of the light signal is disregarded and (b) that more acquisitions need to be performed to get the desired data in comparison to pixels with multiple storage elements and outputs channels (e.g., 2-tap or 4-tap pixels).

Thus the pixel may comprise at least one storage element and one dump element or a plurality of storage elements 42.1, 42.2 for storing or dumping the electric signal.

The four-sample data stack (samples at relatives phases of 0°, 90°, 180° and 270°) is processed by the analysis of the $0^{th}$ and first Fourier coefficient. Other, simplified formalisms for four samples are known. This method offers the readout of two apparent lifetime estimations $\tau_\phi$, $\tau_m$ linked to the phase delays $\phi$ and the demodulations m injected by the finite lifetime of the fluorochrome:

$$\tau_\phi = \omega^{-1} \tan \phi;\ \tau_m = \omega^{-1}(m^{-2}-1)^{1/2}. \quad (1)$$

Here, ω is the circular frequency of the intensity-modulated light source. The two lifetime estimations are related to each other in a manner that depends on the occurrence of excited-state reactions and the presence of lifetime heterogeneity, e.g., caused by the presence of fluorescent species exhibiting different lifetimes as is the case during the occurrence of FRET. The two-sample acquisition (samples at relative phases of 0° and 180°) is analyzed by the rapid lifetime determination algorithm described for FD. This technique enables the measurement of only the demodulation factor:

$$m = \{(I_{0°}-I_{180°})/[2m_0(I_{0°}+I_{180°})]\}^{1/2}, \quad (2)$$

where $m_0$ represents the modulation depth of the light source. The initial relative phase bias between the light source and the detector can partially be compensated by the electronics of the lock-in imager. The residual phase bias, measured using the 4-sample acquisition protocol, was compensated during the computation of the lifetime values. The two-sample acquisition offers a rapid FLIM operation, at the cost of discarding information on possible multi-exponential decay of the fluorochrome.

The sensor of the lock-in imager 4 can be manufactured in 0.8 μm combined CMOS/BCCD semiconductor technology. This allows optimal CCD performance while utilizing the flexibility of the integration of CMOS active-pixel-sensor (APS) readout architectures. The imager chip 4 is composed of an array of 124×160 pixels 40 with an area of approximately 40 μm×55 μm per pixel 40 and with an optical fill factor of approximately 17%. Each lock-in pixel 40 comprises a photosensitive substrate, several CCD gates on top of the photosensitive substrate, two independent charge-storage sites 42.1, 42.32 and an APS readout circuitry. The CCD-gate electrodes 43.1, 43.2 are controlled at opposite phases with a modulation frequency of 20 MHz. This allows the photo-generated electrons to be accumulated in the two different storage sites 42.1, 42.2, depending on the phase instant at which each photon impinges on the sensor 4. Thus, the read-out process of the sensor 4 returns two images that were acquired in parallel at opposite relative phases. The electronics 3 of the lock-in imager sports a USB interface by which its functions and data acquisition is controlled. Therefore, the design of the chip in a standard CMOS/CCD semiconductor technology and the realization of the camera using standard electronic components match the requirements for low-cost and easy-to-use operation.

The preferred embodiment of a pixel 40 of the lock-in imager 4 has a structure that is typical for CCDs. The CCD gate electrodes 43.1, 43.2 are used as transfer means for transferring the photoelectrons from the radiation-sensitive element 41 to a selected storage element 42.1. The stored photo charges are then transferred from the storage element 42.1 to the allocated read-out node 44.1 and read out. Preferably, each pixel 40 can be read out individually, as is known from the CMOS APS technology. As an alternative to the CCD gate electrodes 43.1, 43.2, means for generating a lateral electric drift field at the surface of the pixel 40 can be provided as transfer means. Such drift-field-generating means are known from the prior art and may be designed for instance as a highly resistive layer on the surface of the pixel 40, across which a lateral electric potential is applied.

Figure 4A:
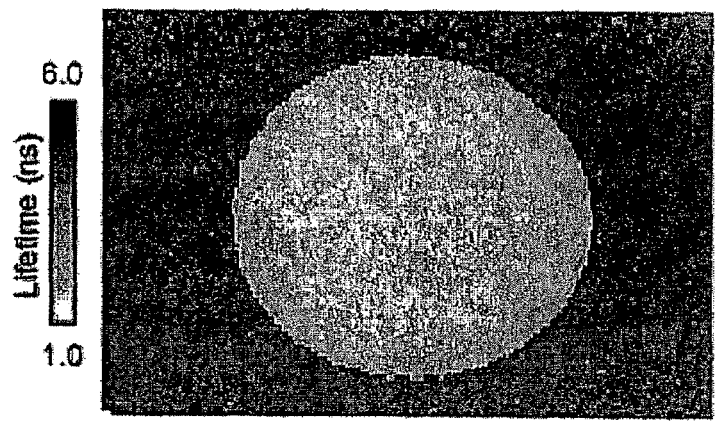
FIG. 4 shows the results of a fluorescence-lifetime measurement made by the FLIM according to the invention.
Figure 4B:
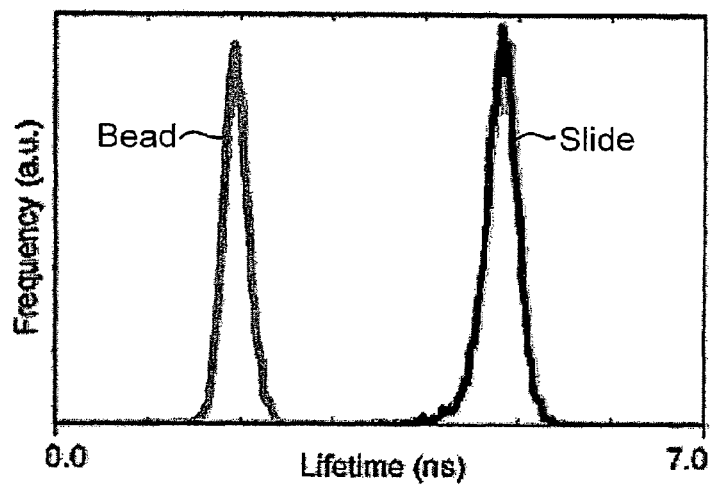

The modulation frequency of 20 MHz is sufficiently high to reliably obtain lifetime images of fluorochromes exhibiting nanosecond lifetimes. For fluorescence detection, the phase delays between the excitation light 20 and the emitted fluorescence 90 are related to the fluorescence lifetime of the fluorochrome (Eq. (1)). FIG. 4 shows lifetime images of a fluorescent Turbo-Sapphire-labeled bead and a fluorescent plastic slide. The system was previously calibrated by the use of a reflective foil positioned in the sample plane as a zero-lifetime control. The fluorescent bead and the plastic slide were imaged sequentially with the acquisition of four phase steps. The excitation light 20 was provided by the laser diode at 405 nm. The overlay of these images and the histograms of their lifetime determinations clearly demonstrate how the camera is able to discriminate between the two different lifetimes.

The major advantages of this lock-in imager design relate to the possibility of simultaneously capturing two modulated images at opposite phases or even four at relative phases of 0°, 90°, 180°, and 270°. Most importantly, this allows lifetime imaging with a single exposure period. The coupling of all-solid-state technology for the detector with LED illumination presents intriguing possibilities. FLIM using LED excitation has been successfully performed on the same system and correctly retrieved the lifetimes of different fluorescent samples with an accuracy and sensitivity similar to the presented experiment using LD excitation. Furthermore, the use of a wide-field detector 4 and the rapid lifetime determination algorithm has been used to perform video-rate imaging at rates of, e.g., 24 Hz.

This invention is not limited to the preferred embodiments described above, to which variations and improvements may be made, without departing from the scope of protection of the present patent. Examples are wide-field sectioning microscopes like Nipkov-disk based confocal microscopes, programmable-array microscopes and the ApoTome or other similar implementations. In another embodiment, lifetime detection according to the invention is coupled to spectrally resolved microscopes to achieve rapid time-resolved spectral imaging.

LIST OF REFERENCE SIGNS

1 Apparatus for imaging
2 Radiation source
20 Excitation radiation
21 Excitation filter
3 Modulation means, control means
4 Lock-in imager
40 Pixel
41 Radiation-sensitive element
42 Storage element
43 Transfer means
44 Readout node
45 Opaque shield
46 Micro-lens array
47 Readout means
51 Collimating lens
52 Microscope lens
53 Optical output port
9 Sample
90 Luminescent radiation

The invention claimed is:

1. An apparatus for imaging a luminescent sample, comprising:
   a radiation source arranged to illuminate the sample with excitation radiation,
   driving electronics for modulating an intensity of the excitation radiation,
   a collimating lens for collimating the excitation radiation,
   a lens for focusing the collimated excitation radiation towards the luminescent sample,
   an optical output port,
   a plurality of pixels arranged behind said optical output port for detecting luminescent radiation emitted by the sample, and
   driving circuitry for controlling the mutual phase relation of the radiation source and said plurality of pixels,
   wherein at least one pixel of said plurality of pixels comprises:
   a radiation-sensitive element for converting incident radiation into an electric signal,
   at least one storage element for storing the electric signal, and
   gate electrodes for transferring the electric signal from the radiation-sensitive element to a selected one of the storage elements, wherein
   the apparatus further comprises: active-pixel-sensor (APS) readout architecture for individually reading out the electric signal stored in the at least one storage element of said at least one pixel.

2. The apparatus according to claim 1, wherein said at least two gate electrodes are connected to said driving circuitry.

3. The apparatus according to claim 1, each gate electrode having a connection for applying an electric potential for generating a lateral electric drift field at a surface of said plurality of pixels.

4. The apparatus according to claim 1, wherein the storage elements are integration gates.

5. The apparatus according to claim 1, wherein said APS readout architecture is allocated to each storage element, and comprise readout lines, each readout line being allocated to a sense node.

6. The apparatus according to claim 1, wherein each pixel of said plurality of pixels comprises at least one storage element.

7. The apparatus according to claim 1, wherein said radiation source, said driving electronics, said plurality of pixels said driving circuitry and said APS architecture are integrated on one single circuit board.

8. The apparatus according to claim 1, further comprising a microscope for imaging the sample onto said plurality of pixels.

9. A method for imaging a luminescent sample, comprising the steps of:
   illuminating the sample with excitation radiation intensity-modulated with a modulation frequency, and
   periodically detecting in a plurality of pixels luminescent radiation emitted by the sample, synchronously with the modulation frequency of the intensity-modulated radiation, characterized in that the detection step comprises the partial steps of:
   converting incident radiation into an electric signal,
   providing at least one storage element in at least one pixel,
   selecting one of the at least one storage element,
   storing the electric signal in said selected storage element,
   wherein the storing of the electric signal is controlled to have a predetermined phase relation with respect to the intensity modulation of the excitation radiation,
   wherein each period of the intensity-modulated radiation is divided into a predetermined number of time intervals,
   wherein one of the at least one storage element is allocated to each time interval, and wherein in each time interval, the electric signal is stored in the storage element corresponding to the actual time interval, and individually reading out the electric signals stored in the at least one storage element of said at least one pixel.

10. The apparatus according to claim 1, wherein said gate electrodes
comprise a connection for applying an electric potential for generating a lateral electric drift field at a surface of said plurality of pixels;
the storage elements are integration gates;
said APS architecture comprising readout lines, each readout line being allocated to a sense node;
each pixel of said plurality of pixels comprises at least one storage element;
the radiation source, said driving electronics, said plurality of pixels, and said APS architecture are integrated on one single circuit board; and wherein
a microscope is provided for imaging the sample onto said plurality of pixels.

11. The method according to claim 9, wherein:
the stored electric signals are read out, and demodulation and/or phase delay parameters are calculated from the electric signals;
the luminescent radiation is decomposed into its spectral components, and at least one of the components is detected so as to obtain information on spectrally-resolved lifetimes of the luminescent radiation.

* * * * *

UNITED STATES PATENT AND TRADEMARK OFFICE
CERTIFICATE OF CORRECTION

PATENT NO.        : 7,508,505 B2
APPLICATION NO.   : 11/490482
DATED             : March 24, 2009
INVENTOR(S)       : Felix Lustenberger et al.

Page 1 of 1

It is certified that error appears in the above-identified patent and that said Letters Patent is hereby corrected as shown below:

On the Title Page, Item (73) Assignees: "Carl Zeiss Microimaging GmPH" should read --CARL ZEISS MicroImaging GMBH--; and On the Title Page, Item (30) Foreign Application Priority Data "05015860" should read --05015860.9--.

Signed and Sealed this

Fourth Day of August, 2009

JOHN DOLL
*Acting Director of the United States Patent and Trademark Office*